(12) United States Patent
Nicholas et al.

(10) Patent No.: US 8,178,740 B2
(45) Date of Patent: May 15, 2012

(54) OLEFIN UPGRADING PROCESS

(75) Inventors: Christopher P. Nicholas, Evanston, IL (US); Laszlo T. Nemeth, Barrington, IL (US); Deng-Yang Jan, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 647 days.

(21) Appl. No.: 12/330,538

(22) Filed: Dec. 9, 2008

(65) Prior Publication Data

US 2010/0145123 A1    Jun. 10, 2010

(51) Int. Cl.
*C07C 2/12* (2006.01)

(52) U.S. Cl. ........ 585/533; 585/254; 585/255; 585/502; 585/520; 585/527; 585/529; 585/530; 585/532

(58) Field of Classification Search ................... 585/500, 585/502, 520, 527, 529, 530, 532, 533, 254, 585/255

See application file for complete search history.

(56) References Cited

U.S. PATENT DOCUMENTS

| | | | | |
|---|---|---|---|---|
| 2,526,966 A | | 10/1924 | Oberfell et al. ................. 196/1 |
| 3,972,832 A | * | 8/1976 | Butter et al. ..................... 502/77 |
| 3,981,941 A | | 9/1976 | Butter ..................... 260/683.15 D |
| 4,254,295 A | * | 3/1981 | Tabak ............................. 585/533 |
| 4,304,948 A | | 12/1981 | Vora et al. ...................... 585/315 |
| 4,393,259 A | | 7/1983 | Ward et al. ..................... 585/315 |
| 4,520,221 A | | 5/1985 | Hsia Chen ...................... 585/517 |
| 4,547,613 A | | 10/1985 | Garwood et al. .............. 585/533 |
| 4,642,404 A | | 2/1987 | Shihabi .......................... 585/415 |
| 4,678,645 A | | 7/1987 | Chang et al. ................... 422/190 |
| 4,716,135 A | * | 12/1987 | Chen ................................ 502/62 |
| 4,749,820 A | | 6/1988 | Kuo et al. ....................... 585/330 |
| 4,788,365 A | * | 11/1988 | Harandi et al. ................ 585/312 |
| 5,049,360 A | | 9/1991 | Harandi et al. ................ 422/141 |
| 5,284,989 A | | 2/1994 | Apelian et al. ................. 585/533 |
| 5,895,830 A | | 4/1999 | Stine et al. ..................... 585/259 |
| 6,080,303 A | * | 6/2000 | Cao et al. .................. 208/120.01 |
| 6,590,132 B1 | * | 7/2003 | Vora ............................... 585/809 |
| 2007/0087934 A1 | * | 4/2007 | R.M. Martens et al. ...... 502/214 |

FOREIGN PATENT DOCUMENTS

| EP | 466305 A2 | * | 1/1992 |
|---|---|---|---|
| GB | 2186287 | | 8/1987 |

OTHER PUBLICATIONS

IZA Database (IZA Database of Zeolite Structures, available at www.iza-structure.org on Jun. 9, 2011).*

* cited by examiner

*Primary Examiner* — In Suk Bullock
*Assistant Examiner* — Bradley Etherton
(74) *Attorney, Agent, or Firm* — Arthur E Gooding

(57) ABSTRACT

A process for the use in the oligomerization of olefins is presented. The process produces a gasoline boiling range product having a high research octane number and almost no aromatics content. The process utilizes a solid catalyst comprising a zeolite that is treated with a phosphorous containing reagent to generate a catalyst having phosphorous content between 0.5 and 15 wt %.

30 Claims, 2 Drawing Sheets

US 8,178,740 B2

OLEFIN UPGRADING PROCESS

FIELD OF THE INVENTION

This invention relates to solid catalysts for the transformation of hydrocarbons. In particular, this invention relates to solid catalysts that oligomerize light olefins to olefins in the gasoline range.

BACKGROUND OF THE INVENTION

The oligomerization of light olefins, such as propylene and butenes, to produce higher carbon number olefins, or olefins having 5 or more carbons is known. The oligomerization process is used for the production of high quality motor fuel from low molecular weight olefins. Oligomerization is also referred to as a catalytic condensation process with a resulting motor fuel often referred to as polymer gasoline, or polygasoline. Methods have been sought to improve the quality of gasoline, and in particular the octane number of the gasoline. This octane enhancement is realized through the improvement in reaction selectivity to enhance the amount of high octane blending components as a result of increasing the amount of branched olefins. Polymer gasoline has the benefit of also being a low aromatic content gasoline.

The current state of the conversion of light hydrocarbons to high octane motor fuels involves the use of strong acid catalysts, such as hydrofluoric acid (HF) catalyst, for the alkylation of light paraffins with olefins. This is commonly referred to as HF alkylation. While HF alkylation has a long history in the production of high octane motor fuels, HF alkylation has significant handling issues, and safety concerns due to the nature of hydrofluoric acid. One alternative is sulfuric acid, but this also present issues, and is also a homogeneous catalytic reaction that requires special handling.

The oligomerization process is often combined with other hydrocarbon transformation processes. Other processes include saturation and dehydrogenation. Patents disclosing the dehydrogenation of light paraffins with oligomerization of the olefinic effluent stream include U.S. Pat. No. 4,393,259, U.S. Pat. No. 5,049,360, U.S. 4,749,820, U.S. Pat. No. 4,304,948, and U.S. Pat. No. 2,526,966.

Hydrotreating of olefinic streams to saturate the olefins to produce a high octane fuel is also known. The oligomerization and hydrogenation of a C4 fraction to produce a jet fuel is disclosed in GB 2,186,287, and which also discloses the optional hydrogenation into a premium gasoline. U.S. Pat. No. 4,678,645 discloses the hydrotreatment of jet fuels, diesel fuels and lubricants that have been produced by dehydrogenation and oligomerization of light paraffins. However, hydrotreating of gasoline produced by oligomerization can reduce octane numbers of the gasoline, while saturating olefins to paraffins.

Other known catalysts for effecting oligomerization include heterogeneous catalysts such as boron trifluoride as described in U.S. Pat. No. 3,981,941, or catalysts that are mild protonic acids, generally having a Hammett acidity function of less than −5.0. Particularly preferred are solid phosphoric acid (SPA) catalysts having as a principal ingredient an acid of phosphorous such as ortho, pyro, or tetraphosphoric acid. SPA catalysts can be found in U.S. Pat. No. 5,895,830.

The use of zeolites for oligomerization, and particularly the use of zeolites having medium pores, is also described in the patent literature. U.S. Pat. No. 4,547,613 uses a ZSM-5 type catalyst that has been conditioned at low pressure and high temperature with a light hydrocarbon gas. A process for producing lubricating oils from the conversion of light olefins using the ZSM-5 catalyst is disclosed in U.S. Pat. No. 4,520,221. Other intermediate pore zeolites are disclosed in U.S. Pat. No. 4,642,404 and U.S. Pat. No. 5,284,989.

While work has indicated that zeolites can be used for the oligomerization of olefins, prior use of zeolites produce a poor quality product for use as a gasoline.

SUMMARY OF THE INVENTION

The present invention provides for a process for the oligomerization of olefins using an improved catalyst. An olefin containing stream, having olefins in the C2 to C12 range is contacted with the improved catalyst at reaction conditions to generate a gasoline product. The gasoline product comprises a mixture of highly branched alkanes, and with almost no aromatics in the product stream. The process utilizes a new catalyst that overcomes the problem of the production of excess heavies. The catalyst comprises a molecular sieve and a binder. The catalyst is treated with a phosphorous reagent, thereby forming a treated catalyst, wherein the resulting treated catalyst has a micropore volume less than 50%, and a crystallinity greater than 50% of the untreated catalyst. The phosphorus reagent can be selected from a phosphate compound, such as phosphoric acid, ammonium phosphate, or diammonium phosphate.

The catalyst utilized in this process comprises a molecular sieve and binder, wherein the molecular sieve is preferably selected from zeolites having a structure from the following structure types: MFI, MEL, ITH, IMF, TUN, FER, BEA, FAU, BPH, MEI, MSE, MWW, UZM-8, MOR, OFF, MTW, TON, MTT, AFO, ATO, or AEL. The molecular sieve pellets are treated with a phosphorous reagent treatment, thereby generating a treated molecular sieve.

Other objects, advantages and applications of the present invention will become apparent to those skilled in the art from the following detailed description.

DETAILED DESCRIPTION OF THE INVENTION

Currently, solid phosphoric acid (SPA) is used in the oligomerization of olefins, and in the alkylation of benzene. SPA is inexpensive and well known, however, it is exceedingly difficult to remove from reactors and is non-regenerable. Therefore, it is desirable to have a regenerable catalyst, and one that is easy to remove from reactors. In the alkylation of benzene, some zeolite based solid catalysts have shown superior performance and life of the catalyst. However, there have been no zeolite materials employed in the commercial scale for the oligomerization of olefins.

The oligomerization of light olefins is performed for the production of a high quality gasoline product, comprising highly branched alkanes and without aromatic compounds, or with very low amounts of aromatic compounds, or aromatics content of less than 1 wt. %. The present invention provides a process for the oligomerization of light olefins in the C2 to C12 range to generate the product known as polymer gasoline, or polygasoline. The light olefins are in an olefin feedstream that is contacted with an improved catalyst under oligomerization reaction conditions for generating the polygasoline product stream. The light olefins are preferably in the C2 to C5 range, and preferably comprise 20 to 100 mol % of the olefin feedstream. Preferably, the product stream will comprise highly branched alkanes and alkenes in the C7 to C12 range.

The oligomerization reaction conditions include operating at a pressure between 2.1 MPa (305 psia) and 10.5 MPa (1520 psia), and preferably at a pressure between 2.8 MPa (405 psia) and 7.6 MPa (1100 psia). The temperature of the oligomerization conditions are in a range between 70° C. and 300° C., and preferably between 90° C. and 200° C.

Figure 1:
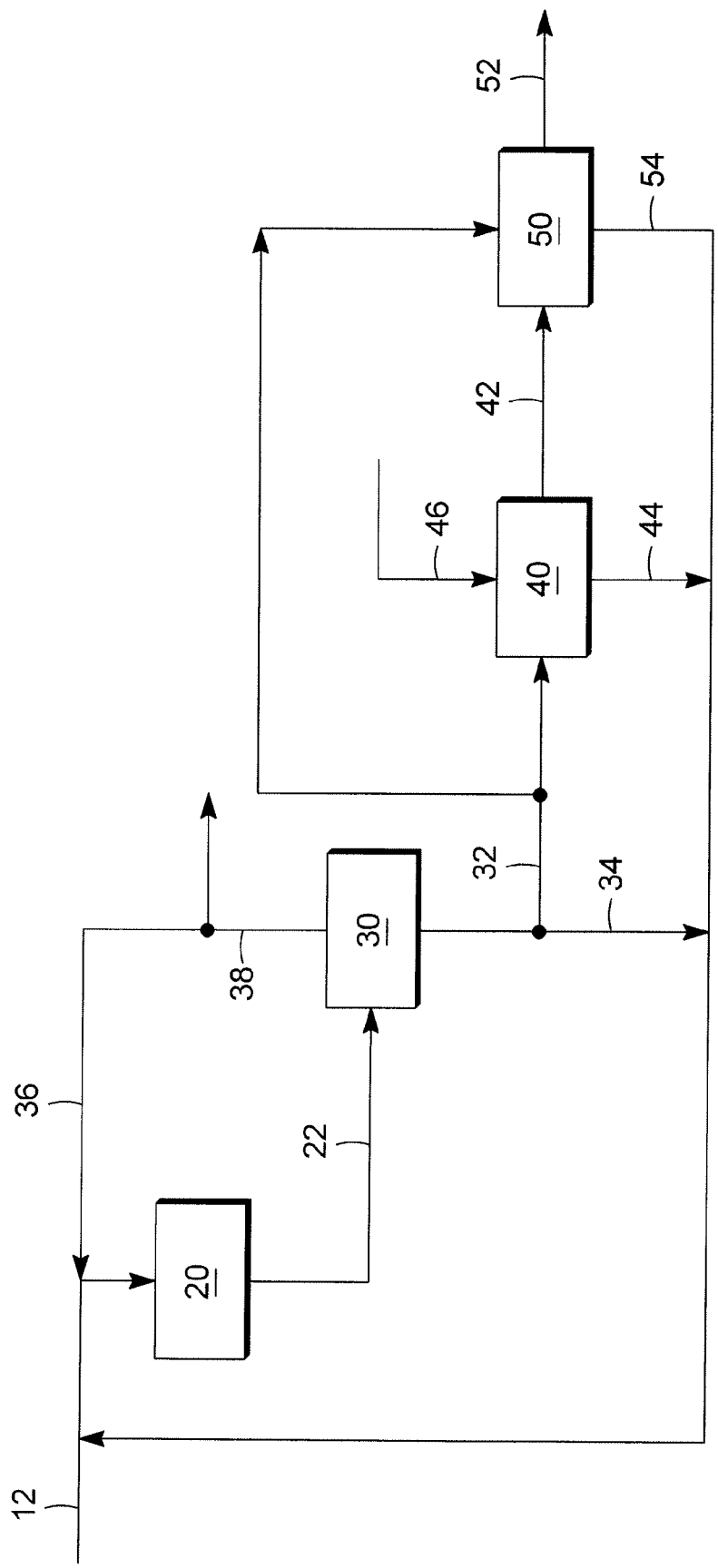
FIG. 1 is a diagram of the process of the present invention.

The process of the present invention comprises oligomerization of light olefins as shown in FIG. 1. A light olefin stream 12, comprising olefins in the C2 to C5 range, is passed to an oligomerization reactor 20, where the olefin reacts under oligomerization conditions to form heavier olefins in an olefin product stream 22. The light olefin stream can be generated by a catalytic cracking process, a process for the dehydrogenation of light paraffins, or from the formation of light olefins through the conversion of oxygenates to olefins. The process is intended to cover any source of light olefins that are converted to heavier olefins for use in a motor fuel.

The olefin product stream 22 is passed to a separation section 30 where the olefin product stream is separated into a heavy stream 32 comprising an olefin product having a molecular weight greater than 72 g/mol, and a light stream 38 comprising an olefin product having a molecular weight less than 72 g/mol. The heavy stream 32 is then passed to a gasoline blending pool 50, thereby creating a liquid product stream 52. In an alternate embodiment, the heavy stream 32 is passed to an olefin saturation unit 40, along with hydrogen 46, where a portion of the olefins in the heavy stream 32 are saturated to form paraffins to form a saturated heavy stream 42. The heavy stream 32 is saturated to increase the amount of branched paraffins, and to increase the motor octane number to at least 85. The saturated heavy stream 42 is then passed to the gasoline blending pool 50.

In another embodiment, a portion 36 of the light stream 38 is passed to the oligomerization reactor 20. The light stream 38 is recycled to increase the yield of heavier components generated by the oligomerization reactor 20. The process also allows for recycle of a portion of the heavy stream 34 to the oligomerization reactor 20, recycling a portion of the saturated heavy stream 44, or a recycling of the liquid product stream 54. The control of recycled liquids can provide control of the oligomerization reaction conditions to improve yields, or to prevent the formation of very large molecules.

The main problem with the use of many zeolites as solid acid replacements for SPA catalysts involves the undesirable production of heavy products. With the oligomerization of olefins, this is a severe problem, especially in the production of hydrocarbons for use in gasoline. With the production of heavies that are generated in the oligomerization process, the heavies go into the gasoline pool and create a poorer gasoline product such as poor drivability.

A solid catalyst for replacing SPA catalyst has been invented, where the catalyst comprises a molecular sieve and a binder. The catalyst is treated with a phosphorous containing reagent to form a treated catalyst that has a micropore volume less than 50% of the untreated catalyst. A micropore volume is the pore volume for pore openings less than approximately 10 Å. The catalyst is further defined as having a crystallinity after treatment to be greater than 50% of the untreated catalyst as measured by X-ray diffraction technique. The catalyst, before treatment, will preferably have an initial micropore volume of at least 0.05 ml $N_2$/g as measured by standardized BET adsorption theory.

Zeolites can be used for oligomerization, and zeolites are more active than SPA for the oligomerization process. The drawback for using zeolites is the increased activity generates a product that contains significant amounts of heavier components with boiling points exceeding gasoline end point specification, or a poorer product. This increases the final boiling point of the product to typically greater than 225° C. The present invention provides for a catalyst that has been treated to modulate the activity of the catalyst and to limit the production of heavies. After treatment of the zeolitic catalyst, the liquid product produced over the catalyst contained only 3 wt % material with a boiling point greater than 225° C. This is comparable to SPA catalyst performance.

The phosphorous treatment of the catalyst produced other benefits. The amount of coking on the catalyst decreased by a factor of 10. This increases the cycle time for operating an oligomerization reactor between catalyst regeneration stages. An important use of the oligomerization of olefins is the production of high octane gasoline, as measured by the octane number, with low aromatic components, or the production of high octane gasoline components for blending with other gasoline. The SPA catalyzed oligomerization produces a product having a research octane number of 98. The product produced by the catalyst of the present invention has a research octane number of 99.

The molecular sieve is preferred to be a zeolite, and where the zeolite comprises between 5 and 95 wt % of the catalyst. Preferred zeolites include zeolites having a structure from one of the following classes: MFI, MEL, ITH, IMF, TUN, FER, BEA, FAU, BPH, MEI, MSE, MWW, UZM-8, MOR, OFF, MTW, TON, MTT, AFO, ATO, and AEL. A most preferred catalyst is MTW.

The catalyst is formed by combining the molecular sieve with a binder, and then forming the catalyst into pellets. The pellets are then treated with a phosphoric reagent to create a molecular sieve having a phosphorous component between 0.5 and 15 wt % of the treated catalyst. This generates a catalyst having a micropore volume less than 50% of the initial micropore volume, while retaining a crystallinity of greater than 50% of the untreated catalyst.

The binder is used to confer hardness and strength on the catalyst. Binders include $Al_2O_3$, $AlPO_4$, $SiO_2$, silica-alumina, $ZrO_2$, $TiO_2$, combinations of these metal oxides, and other refractory oxides, and clays such as montmorillonite, kaolin, palygorskite, smectite and attapulgite. A preferred binder is an aluminum based binder, such as $Al_2O_3$, $AlPO_4$, silica-alumina and clays, wherein a portion of the binder is converted to $AlPO_4$ during the phosphorous treatment process.

The phosphorous reagent is preferably a phosphate compound, and is preferably selected from phosphoric acid ($H_3PO_4$), ammonium phosphate ($NH_4H_2PO_4$), and diammonium phosphate (($NH_4)_2HPO_4$). A most preferred compound is phosphoric acid. Other phosphorous containing reagents include triphenyl phosphine, trialkyl phosphines, trialkyl phosphites, and phosphorous oxytrichloride. The catalyst is contacted with the phosphorous containing reagent for a treatment time between 1 hour and 10 hours. The treatment is run for a sufficient time to achieve a phosphorous level between 0.5 and 15 wt % of the treated catalyst. Preferably, the phosphorous level is between 5 and 12 wt % of the treated catalyst.

The catalyst is treated with the phosphorous reagent at a temperature between 20° C. and 100° C., and preferably at a temperature between 60° C. and 80° C. The treated catalyst is then subjected to a calcining treatment at a temperature greater than 300° C.

The catalyst formed preferably comprises a one-dimensional molecular sieve. A one-dimensional molecular sieve contains non-intersecting pores that are substantially parallel to one of the axes of the crystal. The pores preferably extend through the zeolite crystal. The pores preferably are comprised of either 10 or 12 membered rings.

In a preferred embodiment, the catalyst comprises a zeolite having an MTW structure, which when treated with a phosphorous reagent produces a catalyst that, when used in olefin oligomerization, generates a high quality product having a low heavies selectivity.

In an alternate embodiment, the catalyst can be produced by treating the zeolite with a phosphorous reagent to create a zeolite having a phosphorous content between 0.5 and 15 wt % of the treated zeolite. The treated zeolite is then mixed with a binder, and then formed into pellets. The pellets are then calcined to harden the pellets and drive off any water, thereby creating the treated catalyst.

TABLE 1

Product Selectivity

| Catalyst/selectivity | SPA | 80/20 MTW/Al$_2$O$_3$ | 10% P H$_3$PO$_4$ MTW/Al$_2$O$_3$ | 70/30 UZM-8/Al$_2$O$_3$ | 10% P H$_3$PO$_4$ UZM-8/Al$_2$O$_3$ |
|---|---|---|---|---|---|
| C5 selectivity | 1.3 | 0.3 | 0 | 0.8 | 0.5 |
| C6 selectivity | 7.9 | 2.2 | 0.4 | 2.1 | 1.5 |
| C7 selectivity | 33.0 | 25.6 | 14.0 | 15.6 | 18.6 |
| C8 selectivity | 23.4 | 23.3 | 24.1 | 21.9 | 25.2 |
| C9/C10 select. | 23.9 | 16.3 | 4.9 | 16.2 | 12.1 |
| C10-12 select. | 7.5 | 17.3 | 53.6 | 13.4 | 20.1 |
| Heavies select. | 3.0 | 15.0 | 3.0 | 30.0 | 22.0 |

The results in Table 1, show the product selectivity for the new phosphorous treated catalyst as compared with the untreated catalyst. The product from the SPA catalyst is included for comparison. The phosphorous treated catalyst shows a decline in the heavies content over the untreated catalyst. When the catalyst is MTW/Al$_2$O$_3$, the heavies content decreased to be comparable with the heavies content of the SPA catalyst. There was also a shift in selectivities with the phosphorous treated catalyst. There was an increase in branched C12 compounds, in particular triisobutylene. Branched alkenes are good for increasing octane numbers. In addition, utilizing the phosphorous treated catalyst causes a reduction in the selectivity to the C5 fraction of the gasoline. It is beneficial to minimize the amount of C5 and C6 compounds in the gasoline pool due to the increase in Reid vapor pressure they cause.

A sample of alumina bound MTW extrudate of 1/16" diameter was treated with phosphoric acid. A solution was made using 27.5 gm of 85% H$_3$PO$_4$ with 485.7 gm of deionized water in a flask. A sample comprised 57 gm of alumina bound MTW extrudate was added to the flask, and the flask was attached to a rotary evaporator. The molecular sieve was reacted with the phosphoric acid solution at 70° C. and the flask was rotated until most of the interstitial liquid was gone. A 10% P on MTW zeolite was obtained.

The MTW extrudate included an alumina binder. The catalyst, after treatment with phosphoric acid was then calcined at 350° C. to drive off any residual water. The extrudate was formed as 1/16" extrudate pellets.

The phosphorus treated zeolite was loaded into a steel reactor, and a process stream was passed over the catalyst at reaction conditions to form a gasoline product. The process stream was a 50:50 mixture of C3 and C4, with the olefin to paraffin ratio equal to 50:50 for both C3 and C4. The reactor was operated at 3.5 MPa (500 psi) with weight hourly space velocities (WHSV) between 1.0 and 5.0 hr$^{-1}$. The temperature for the reaction in the bed was between 110° C. and 130° C., but because the reaction is exothermic, the furnace temperature is usually 10-20° C. less. The choice of feedstock for the process stream is simply a model feedstock that is similar to many feeds for commercial units that use SPA catalyst, and not intended to be limiting. Other feedstocks containing light olefins can also be used.

Example 1. A sample of MTW zeolite was bound with Al$_2$O$_3$ at 80/20 ratio. Example 2. The catalyst of Example 1 was treated with H$_3$PO$_4$ to give a catalyst containing 1 wt % P. Example 3. The catalyst of Example 1 was treated with H$_3$PO$_4$ to give a catalyst containing 5 wt % P. Example 4. The catalyst of Example 1 was treated with H$_3$PO$_4$ to give a catalyst containing 10 wt % P. Example 5. The catalyst of Example 1 was treated with (NH$_4$)H$_2$PO$_4$ to give a catalyst containing 10 wt % P. Example 6. A sample of UZM-8 was bound with Al$_2$O$_3$ at 70/30 ratio. Example 7. The catalyst of Example 6 was treated with H$_3$PO$_4$ to give a catalyst containing 10 wt % P. Example 8. A sample of MTT zeolite was bound with Al$_2$O$_3$ at 80/20 ratio. Example 9. The catalyst of Example 8 was treated with H$_3$PO$_4$ to give a catalyst containing 10 wt % P.

TABLE 2

Catalyst Characterization

| Catalyst | BET SA (m$^2$/g) | N$_2$ Pore Vol. (mL/g) | Relative Crystallinity | P content (wt %) |
|---|---|---|---|---|
| Example 1. | 280 | 0.368 | Reference | 0 |
| Example 2. | 244 | 0.333 | 91 | 1 |
| Example 3. | 117 | 0.163 | 76 | 5 |
| Example 4. | 25 | 0.069 | 86 | 10.1 |
| Example 5. | 28 | 0.063 | 72 | 10.2 |
| Example 6. | 424 | 0.728 | Reference | 0 |
| Example 7. | 122 | 0.302 | N/A | 11.2 |
| Example 8. | 129 | 0.319 | Reference | 0 |
| Example 9. | 15 | 0.072 | 64 | 10.1 |

One can see from Examples 1-4 that after treating a MTW catalyst to between 5 and 12 wt % phosphorous content with H$_3$PO$_4$ that surface area and micropore volume of the catalyst are decreased to less than 50% of the initial value, while unexpectedly retaining >50% of crystallinity relative to the catalyst of example 1. Example 1 catalyst has an N$_2$ micropore volume of 0.07 mL/g, and example 4 catalyst has an N$_2$ micropore volume of 0.005 mL/g as determined by t-plot analysis of the N$_2$ BET data. By comparing examples 1, 4 and 5, one can see that varying the phosphorous reagent at constant phosphorous content has a secondary effect on both surface area and relative crystallinity. In examples 8 and 9, another 1-dimensional zeolite, MTT, is studied. Treating the catalyst of example 8 with H$_3$PO$_4$ causes a reduction in surface area and pore volume while retaining zeolite crystallinity. Examples 6 and 7 show the effect of the same treatment on a multi-dimensional zeolite, UZM-8. Treatment of a UZM-8 catalyst also shows greater than 50% reduction in surface area and pore volume while retaining greater than 50% crystallinity relative to the untreated sample.

Figure 2:
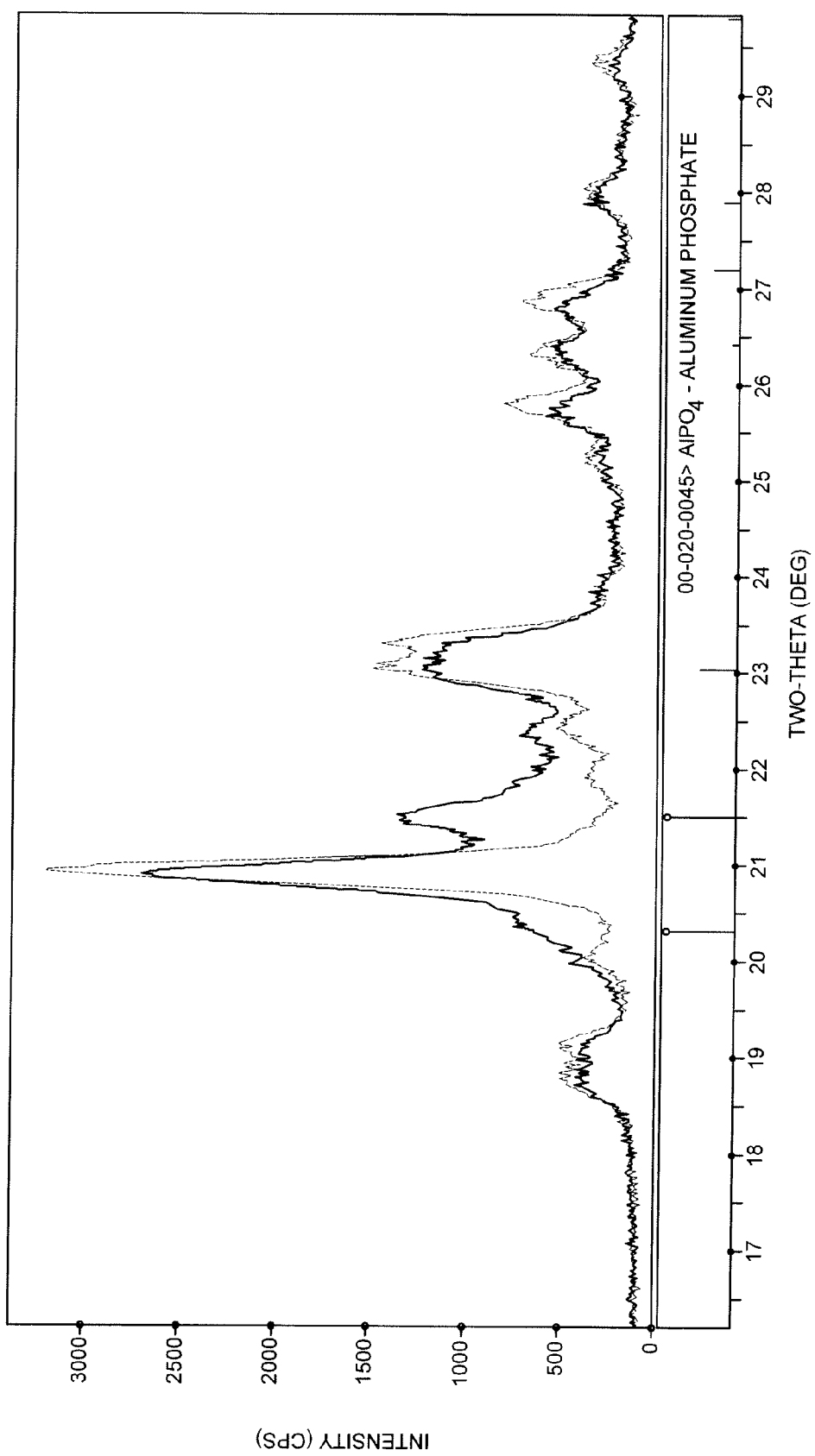
FIG. 2 is an x-ray diffraction pattern of the catalyst of example 1 (dashed line) and example 4 (solid line) showing the transformation of $Al_2O_3$ binder to $AlPO_4$.

The x-ray diffraction pattern of the catalyst of example 1 and example 4 are presented in FIG. 2. The overall crystallinity was not affected significantly by the incorporation of phosphorus. As can be seen by the appearance of the peaks at d=4.370 Å and 4.130 Å in the catalyst of example 4, a portion of the Al$_2$O$_3$ binder is converted to AlPO$_4$ during the phosphorous treatment.

An MTW zeolite was used for oligomerization, but produced a product comprising 15 wt. % heavies. The heavies having a boiling point greater than 225° C. are undesirable for a gasoline product. Utilizing a P treated MTW zeolite to moderate the catalyst activity, and to reduce the heavies production, the oligomerization process was run. The results from the oligomerization using the P treated zeolite generated only 3 wt. %  heavies. A significant improvement over the untreated zeolite.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the oligomerization of an olefin containing feed, comprising: contacting the olefin containing feed at oligomerization conditions, having olefins in the range from C2 to C12, with a solid catalyst at reaction conditions thereby forming a polygasoline product comprising highly branched alkenes, wherein the catalyst comprises a zeolite and a binder, wherein the zeolite has a structure selected from the group consisting of MFI, MEL, ITH, IMF, TUN, FER, BEA, FAU, BPH, MEI, MSE, MWW, UZM-8, MOR, OFF, MTW, TON, MTT, AFO, ATO, and AEL, and mixtures thereof, wherein the catalyst has been treated with a phosphorous containing reagent selected from the group consisting of phosphate compounds, phosphite compounds, phosphorus oxytrichloride, and mixtures thereof, thereby forming a treated catalyst having a micropore volume less than 50%, and a crystallinity greater than 50% of the untreated catalyst.

2. The process of claim 1 wherein the oligomerization conditions include a pressure between 2.1 MPa (305 psia) and 10.5 MPa (1520 psia).

3. The process of claim 2 wherein the oligomerization conditions include a pressure between 2.8 MPa (405 psia) and 7.6 MPa (1100 psia).

4. The process of claim 1 wherein the oligomerization conditions include a temperature between 70° C. and 300° C.

5. The process of claim 4 where the olefin oligomerization is carried out at a temperature of between 90° C. and 200° C.

6. The process of claim 1 where the olefin content comprises light olefins, in the C2 to C5 range, between 20 mol % and 100 mol % of the total feed.

7. The process of claim 1 wherein the polygasoline product has a research octane number of at least 90.

8. The process of claim 1 wherein the polygasoline product has an aromatics content of less than 1 wt %.

9. The process of claim 1 wherein the polygasoline product comprises highly branched alkanes and alkenes in the C7 to C12 range.

10. The process of claim 1 wherein the zeolite comprises between 5 and 95 wt. % of the catalyst.

11. The process of claim 1 wherein the zeolite has an MTW structure or a UZM-8 structure.

12. The process of claim 1 wherein the zeolite comprises non-intersecting pores that are substantially parallel to one of the crystal axes, and the pores extend through zeolite crystal.

13. The process of claim 12 wherein the zeolite is from the MTW structure type.

14. The process of claim 1 wherein the phosphorous containing reagent is selected from the group consisting of phosphoric acid ($H_3PO_4$), ammonium phosphate ($NH_4H_2PO_4$), diammonium phosphate (($NH_4)_2HPO_4$), trialkyl phosphites, and mixtures thereof.

15. The process of claim 14 wherein the phosphorous containing agent is phosphoric acid.

16. The process of claim 1 wherein the phosphorous content of the treated catalyst is between 0.5 and 15 wt %.

17. The process of claim 16 wherein the phosphorous content of the treated catalyst is between 5 and 12 wt %.

18. The catalyst of claim 1 wherein the binder material is selected from the group consisting of $Al_2O_3$, $AlPO_4$, $SiO_2$, silica-alumina, $ZrO_2$, $TiO_2$, montmorillonite, kaolin, palygorskite, smectite, attapulgite, and mixtures thereof.

19. The process of claim 18 wherein the binder material is alumina.

20. The process of claim 18 wherein a portion of the binder material is converted to $AlPO_4$ during the phosphorous treatment process.

21. A process for the oligomerization of an olefin containing feed, comprising: contacting the olefin containing feed, having olefins in the range from C2 to C5, with a solid catalyst at oligomerization reaction conditions, in an oligomerization reactor, thereby forming an intermediate olefin stream containing a highly branched olefin product having a molecular weight greater than 72 g/mol, wherein the catalyst comprises a zeolite and an $Al_2O_3$ binder, wherein the zeolite has a structure selected from the group consisting of MFI, MEL, ITH, IMF, TUN, FER, BEA, FAU, BPH, MEI, MSE, MWW, UZM-8, MOR, OFF, MTW, TON, MTT, AFO, ATO, and AEL, and mixtures thereof, wherein the catalyst has been treated with a phosphorous containing reagent selected from the group consisting of phosphate compounds, phosphite compounds, phosphorus oxytrichloride, and mixtures thereof, thereby forming a treated catalyst having a micropore volume less than 50% of the untreated catalyst, and a crystallinity greater than 50% of the untreated catalyst.

22. The process of claim 21 further comprising passing the intermediate olefin stream to a separation section thereby creating a light stream comprising components having a molecular weight less than 72 g/mol and a heavy stream comprising components having a molecular weight greater than 72 g/mol.

23. The process of claim 22 wherein at least a portion of the heavy stream is passed through an olefin saturation unit to increase the motor octane number of the heavy stream to at least 85, thereby generating a saturated heavy stream.

24. The process of claim 23 wherein the saturated heavy stream is passed to a gasoline blending pool.

25. The process of claim 24 wherein at least a portion of the saturated heavy stream is recycled back to the oligomerization reactor.

26. The process of claim 22 wherein a portion of the heavy stream is passed back to the oligomerization reactor section.

27. The process of claim 22 wherein at least a portion of the light stream is passed to the oligomerization reactor section.

28. The process of claim 21 wherein a portion of the olefin containing feed is passed from a catalytic cracking process.

29. The process of claim 21 wherein a portion of the olefin containing feed is passed from a unit for the dehydrogenation of C2 to C5 paraffins.

30. The process of claim 21 wherein a portion of the olefin containing feed is passed from a unit for the conversion of oxygenates to olefins.

* * * * *